United States Patent [19]

Sans

[11] Patent Number: 5,312,348

[45] Date of Patent: May 17, 1994

[54] SINGLE-USAGE DISPOSABLE HYPODERMIC SYRINGE

[76] Inventor: Ten S. Sans, 2F, No. 17, Alley 13, Lane 2, Chung-Sun Rd., Sec, 2,, Chung-Ho City, Taipei, Taiwan

[21] Appl. No.: 124,414

[22] Filed: Jul. 30, 1993

[51] Int. Cl.⁵ .............................................. A61M 5/00
[52] U.S. Cl. .................................... 604/110; 604/220
[58] Field of Search ................ 604/110, 187, 218, 220

[56] References Cited

U.S. PATENT DOCUMENTS

| | | | |
|---|---|---|---|
| 4,233,975 | 11/1980 | Yerman | 604/110 |
| 4,252,118 | 2/1981 | Richard et al. | 604/110 |
| 5,000,735 | 3/1991 | Whelan | 604/110 |

*Primary Examiner*—John D. Yasko

[57] ABSTRACT

A single-usage disposable hypodermic syringe in which the needle cover of the conventional syringe is replaced by a tubular housing which encloses from the tip of the needle cannula to the rear end of the barrel. An empty space is reserved inside the needle locking base for the positioning of a plug. When an arc segment of a projected member located at the front of the plunger is moved forward with the plunger, the plug with the channel is being pushed to the bottom of the empty space, allowing the plug to rotate and block off the opening of the needle cannula. The medication can no longer be given. A triangular plate installed in the rear portion of the Y-shaped plunger is used to restrict the movement of the projecting plate. Only when the projecting plate is rotated and swing away that the syringe is able to accept medication. The syringe cannot be reused and the tubular housing is used to cover the overall syringe for disposal.

6 Claims, 4 Drawing Sheets

SINGLE-USAGE DISPOSABLE HYPODERMIC SYRINGE

BACKGROUND OF THE INVENTION (a) Field of the Invention

The present invention relates to a hypodermic syringe, particularly to a syringe which can only be used once and absolutely cannot be reused.

(b) Description of the Prior Art

Our understanding of how the body works has broadened rapidly in recent years, paralleled by equally dramatic improvements in medical technology. As a result of this progress, a person's chances of staying healthy into old age depend increasingly on following expert advice and making full use of preventive technique such as vaccination. Therefore, the hypodermic syringe used for vaccination is getting a lot of attention. It is demanded that the syringe shall be disposed after each use. However, it hard to tell whether the syringe is brand new of have been used before. In order to assure that the conventional syringe cannot be reused on another patient for safety reason, improvements to the existing syringe needs to be developed.

SUMMARY OF THE INVENTION

The main object according to the present invention is to provide a new structure for a hypodermic syringe such that it cannot be reused after one injection.

Another object according to the present invention is to provide a new structure for a hypodermic syringe such that there is no safety concern when disposed and will not cause injury to the personnel handling the disposed syringe.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

Figure 1:
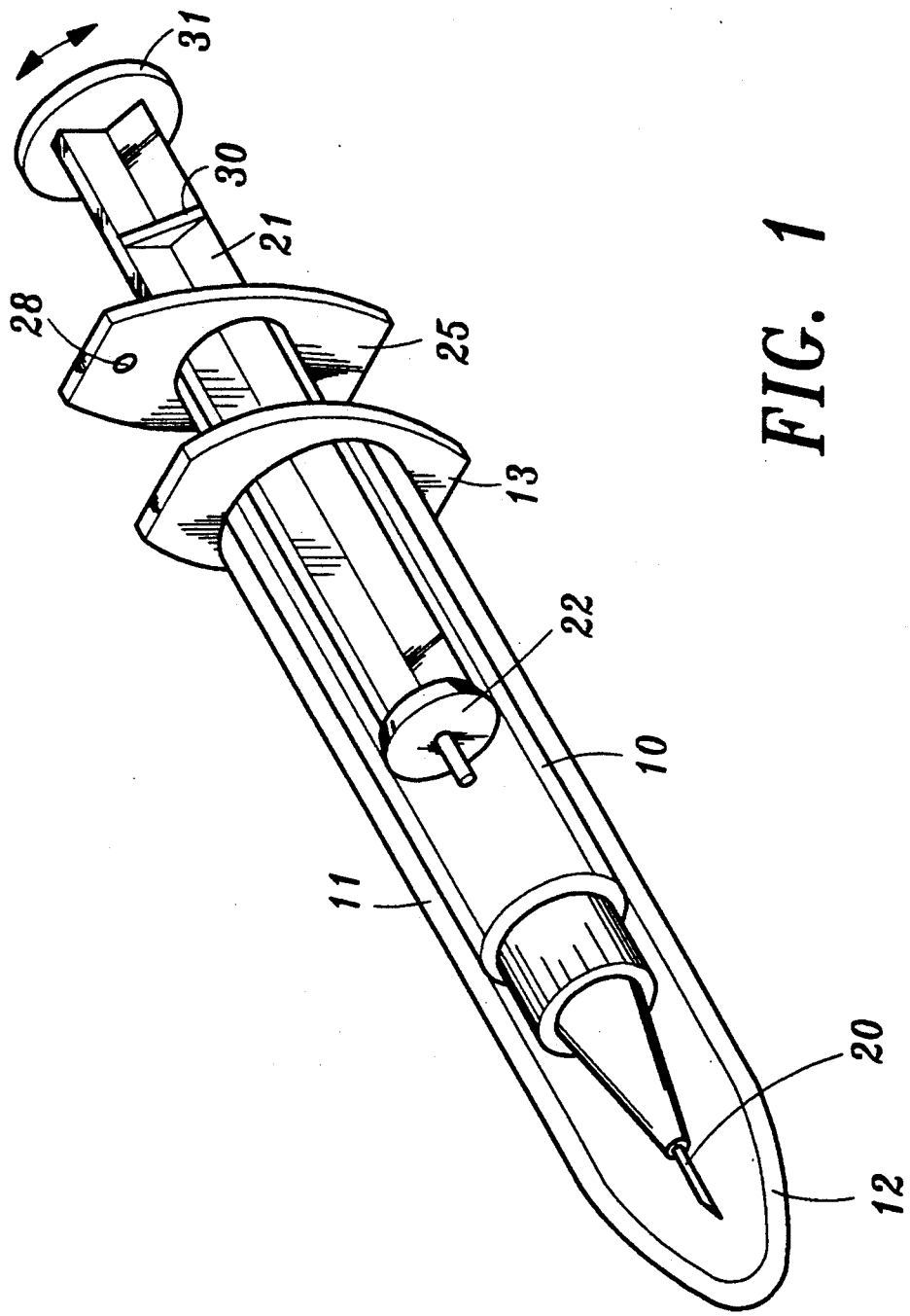
FIG. 1 is a perspective view of the single-usage disposable syringe according to the present invention.

Referring to FIG. 1, which shows a perspective view of an assembly of the single-usage disposable syringe according to the present invention. The needle cover of the conventional syringe is being replaced by a tubular housing 11 which encloses the rear end of the barrel 10. The length of the tubular housing 11 extends from the tip of the needle cannula to the rear end of the barrel 10 and snaps at an appropriate location. The front of the tubular housing is a cone shape and the rear end of which is a finger flange 13. The needle base of the syringe is generally small and it is not easy to insert the needle cannula back into the needle cover after use. This is why the new structure has the tubular housing replacing the conventional needle cover. Another purpose of the tubular housing 11 is that it is part of the syringe assembly and is therefore safe to dispose after use. On the other hand, the needle cover and the syringe are two different parts. If the syringe is disposed without a needle cover on it, it can cause injury to the cleaning personnel.

Figure 2:
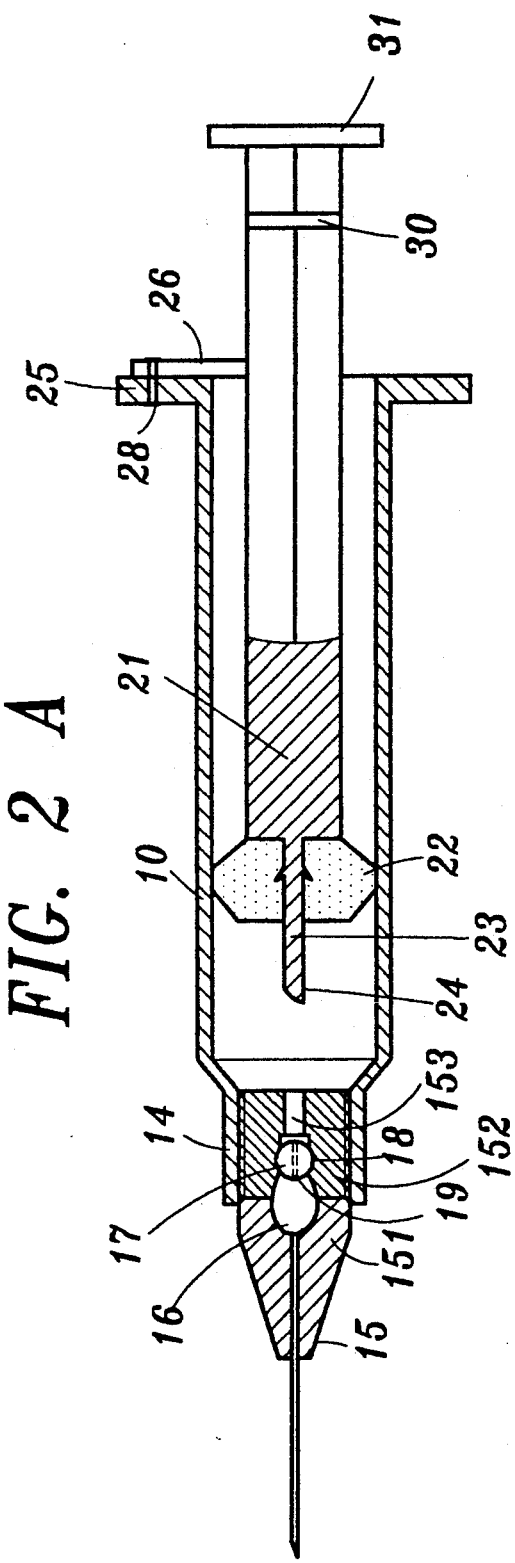
FIG. 2A is a cross-sectional diagram of the first embodiment of the syringe before injection according to the present invention.
FIG. 2B is a cross-sectional diagram of the first embodiment of the syringe after injection according to the present invention.
FIG. 2C is a cross-sectional diagram of the second embodiment of the syringe before injection according to the present invention.
FIG. 2D is a cross-sectional diagram of the second embodiment of the syringe after injection according to the present invention.
Figure 2:
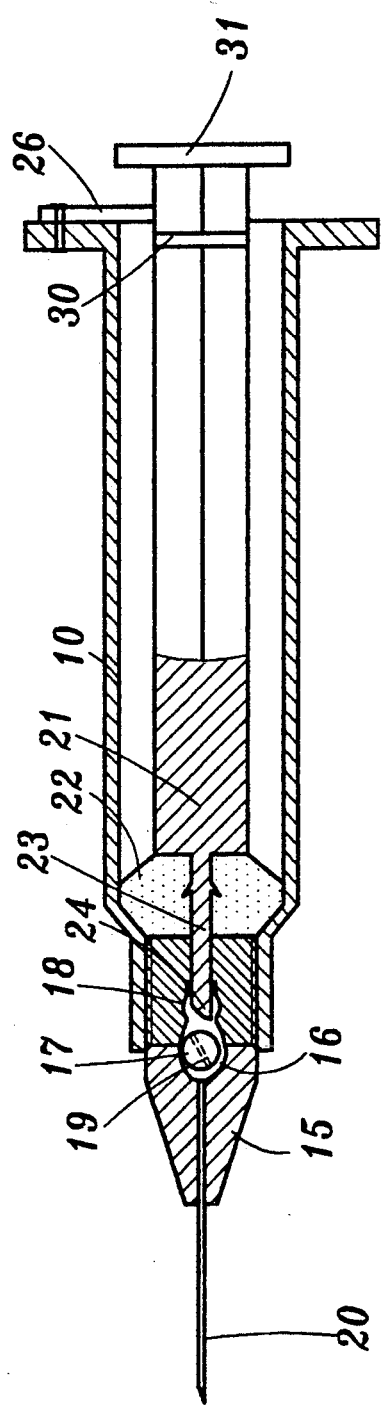
Figure 2:
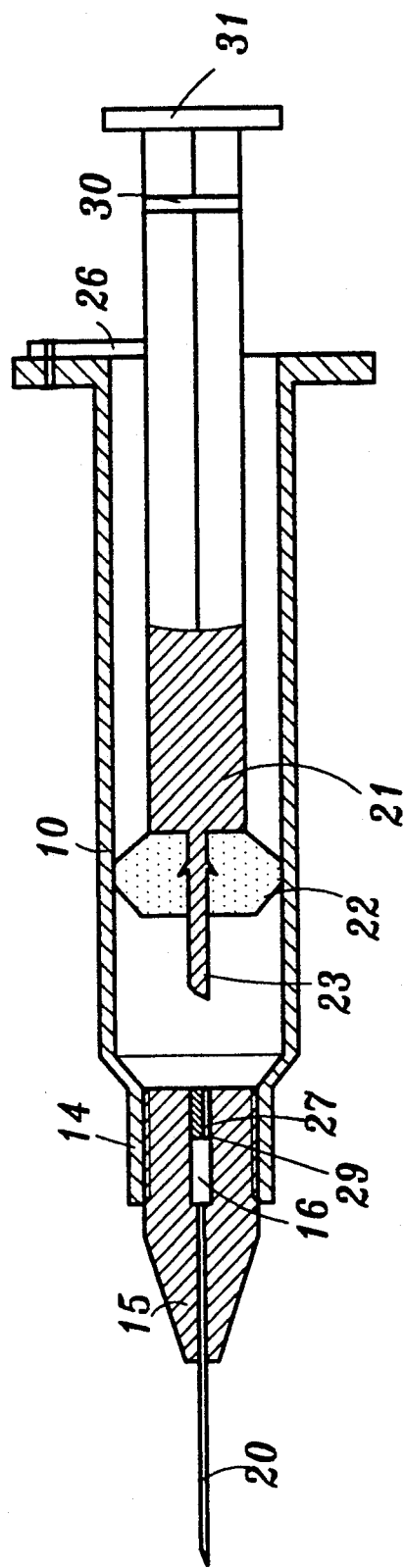
Figure 2:
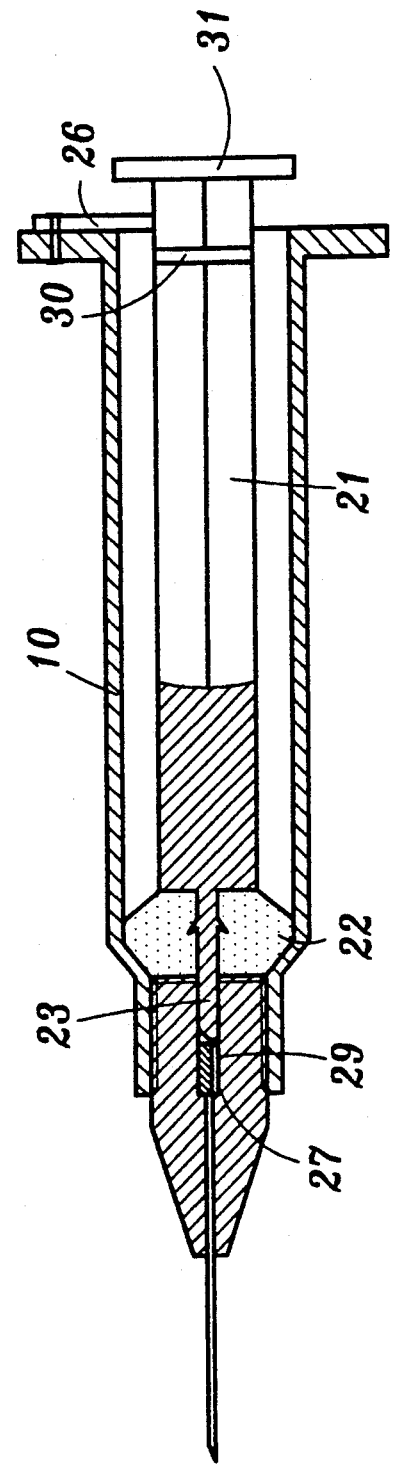

The attachment of the needle cannula to the barrel of the syringe according to the present invention is different from the conventional one. An empty space 16 is reserved inside the needle locking base 15, as is shown in the two embodiments in FIG. 2. Referring to FIG. 2A, a ball plug 17 is fixed in a position inside the empty space 16. This divides the needle locking base 15 into two pieces, the upper base 151 and the lower base 152. The reason of this dividing is because the ball plug 17 must be located inside a position formed by a base 18. The base 18 is centrally located inside the lower base 152, allowing the ball plug 17 be smoothly placed in an appropriate position from the top of the lower base 152. The empty space alone is not appropriate to place the ball plug 17. The lower base 152 is directly connected to the internal space of the barrel 10 through a channel 153 which is smaller in diameter than the ball plug 17. The lower base 152, based on its shape and function, may be considered as an annular plug with male screw threads. Therefore, the male screw threads of the lower base is used to screw into the female screw threads in a connecting base 14 which is located in the tapered end of the barrel 10. Part of the upper base 151 is attached to the needle cannula while the other part forms the elliptic-shaped empty space 16. The male screw threads in the lower portion of the upper base 151 is also screwed into the female threads of the connecting base 14. Accordingly, the needle cannula is now attached to the upper base 151, through which the connecting base 14, the lower base 152 and the barrel 10 are all connected together to form the single-usage syringe.

The channel opening 19 is opened at the center of the ball plug 17. The channel opening 19 is set to face the opening of the needle cannula 20 and parallel to the needle cannula when the ball plug 17 is placed in. In addition, a rubber plug 22 located at the front end of the plunger 21, is connected to a projected member 23 in a direction pointing to the needle cannula 20. The external of the projected member 23 is an arc segment 24. As the plunger is pushed forward, the projected member 23 also advances and drives into the channel 153 of the lower base 152. The projected member 23 continues to progress inside the narrow channel 153 until the segment 24 of the projected member 23 touches the ball plug 17 and seals its channel opening 19. No more medication can be injected accordingly. However, the arc segment 24 is in contact with the lower portion of the ball plug 17 and pushes it away from the base 18. This allows the ball plug to rotate itself into the empty space 16 of the upper base 15. At this time the channel opening 19 is tilted and is no longer facing the needle cannula 20, as is shown in FIG. 2B. If a flat surface were in direct contact with the ball plug, the plug would only move forward and the channel opening would still facing the needle cannula. Therefore, the empty space 16 is appropriately design such that part of the ball plug 17 seals off the channel of the needle cannula. This accomplishes the injection process and the syringe can no longer be reused because the channel has been sealed. The shape of the rubber plug 22 is preferably made to match the upper part of the barrel and snap onto the plunger. The projected member of the plunger ensures that the rubber plug is secured with the plunger. In addition, the rubber plug is made to be able to slide smoothly inside the plunger.

FIG. 2C shows a simplified version of the syringe according to the present invention. There are some differences as compared to the one in FIG. 2A. The needle locking base 15 is no longer be divided into two pieces and the empty space 16 is forming the shape of a hollow post. The channel 153 is still connected to the inside of the barrel. The rear portion of the empty space 16 is modified to have a post plug 27 which also has a channel opening 29. Such channel opening is offset from the center of the post plug 27. When the projected member 23 moves forward, it pushes the post plug 27 into the front part of the empty space 16 and seals off the channel to the needle cannula.

Figure 3:
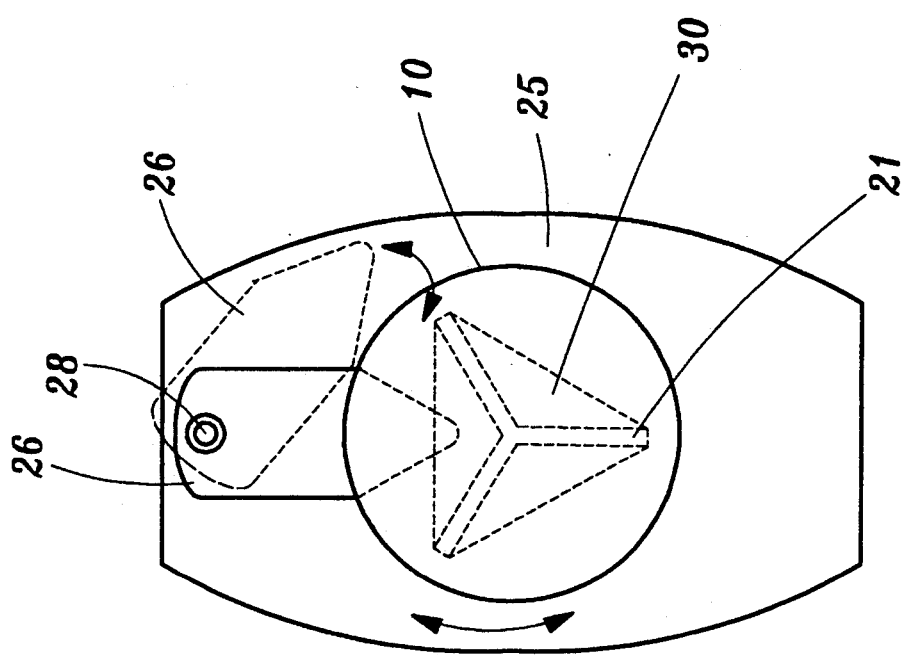
FIG. 3 is a side view of the projected plate in the rear half section of the syringe according to the present invention.

In general, the medication to be injected has to be sucked in first. To avoid the plunger from being mistakenly used, such as the plug being pushed first and loses its primary function, a safety device has to be installed. Hence, a sharp projecting plate 26 is mounted on a pivot 28 on the edge of the finger flange 25, as is shown in FIG. 3. The projecting plate 26 is a small square plate having a sharp end pointing at the barrel. The length of the projecting plate 26 mounted on the pivot 28 is able to shield the plunger partially but does not affect its forward movement. Therefore, the plunger 21 of the syringe according to the present invention is made to have a "Y" shape. Also, in the rear portion of the plunger a triangular plate 30 is installed. When the syringe is not used, the projecting plate 26 is facing towards the center of the plunger. During the process of injection, the projecting plate 26 is restricted by the triangular plate 30 and cannot move forward. Only when the projecting plate 26 is rotated and swing away that the syringe is able to accept medication. Therefore, the plunger is opened up to accept medication and the air bubbles are squeezed out so that the injection can be carried out. Accordingly, the projecting plate 26 is rotated outward at an angle as shown in the dotted lines in FIG. 3. Now the syringe is ready to be used for injection and it can only be used once. The tubular housing 11 is used to cover up the needle cannula and the syringe is ready to be disposed. This syringe cannot be reused because the injection channel is blocked. It is costly to take it apart and clear up the channel. The labor cost is actually higher than the material cost. Also, the assembly uses screw threads for a description purpose only, it can be secured together by use of ultrasound or glue on and the non-reusable feature of the syringe is not affected.

Because the ball plug 17 is located inside the appropriate position formed by base 18, it is impossible for the ball plug 17 to slide due to the pressure applied during injection. In addition, the post plug 27 is secured by a slanted conical hole. All these are designed for the purpose of mi-handling. The needle cannula itself is open to the channel opening so the medication can be injected properly.

The foregoing description of the preferred embodiment of the invention has been presented for the purpose of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A single-usage disposable hypodermic syringe comprising a needle cannula, a needle locking base, a barrel, a plunger and a finger flange wherein:

a tubular housing encloses from the tip of the needle cannula to the rear end of the barrel and snaps at an appropriate location, the front of the tubular housing is a cone shape and the rear end of which is a finger flange; an empty space is reserved inside the needle locking base, a ball plug is fixed inside the empty space in an appropriate position, from where the internal space of the barrel is connected to through a channel which is smaller in diameter than the ball plug, the needle locking base is securely mounted on a connecting base which is located in the tapered end of the barrel; a channel opening, which joins with the empty space, is opened at the center of the ball plug, said empty space is linked to the channel of the needle cannula, a rubber plug located at the front end of the plunger, is connected to a projected member in a direction pointing to the needle cannula, as the plunger is pushed forward, the projected member also advances and is driven into the channel, the projected member continues to move inside the channel until the dosage of medication is finished, at this time the projected member is in contact with the ball plug and blocks the channel opening, no more medication can be injected accordingly, the empty space is appropriately designed such that the ball plug seals off the channel to the needle cannula and therefore the syringe can no longer be reused, the shape of the rubber plug is preferably made to match the upper part of the barrel and snap onto the plunger, the projected member of the plunger ensures that the rubber plug is secured with the plunger, the rubber plug is made to be able to slide smoothly inside the plunger; to avoid the plunger from being mistakenly used, such as the plug being pushed first and the plunger loses its primary function, a projecting plate is mounted on a pivot on the edge of the finger flange, the projecting plate is a small square plate having a sharp end pointing at the barrel, the length of the projecting plate is able to shield the plunger partially but does not affect its forward movement, the plunger is made to have a "Y" shape and in the rear portion of the plunger a triangular plate is installed, when the syringe is new, the projecting plate is facing toward the center of the plunger, the projecting plate is restricted by the triangular plate and cannot move forward during injection, only when the projecting plate is rotated that the syringe is able to accept medication, the tubular housing is used to cover up the needle cannula and the syringe is ready to be disposed.

2. A syringe as recited in claim 1 wherein the needle locking base has a ball plug which is securely attached to a base, the needle locking base is divided into an upper base and a lower base, said base is centrally located inside the lower base, allowing the ball plug to be smoothly placed in an appropriate position from the top of the lower base, the lower base is directly joint to the internal space of the barrel through a channel which is smaller in diameter than the ball plug, the male screw threads of the lower base is used to screw into the female screw threads in a connecting base, part of the upper base is attached to the needle cannula while the other part forms the elliptic-shaped empty space, the male screw threads in the lower portion of the upper base is also screwed into the female threads of the connecting base, a channel opening is opened at the center of the ball plug, the channel opening is set to face the needle cannula when the ball plug is placed; the external of the projected member is an arc segment, when such arc segment touches the bottom of the ball plug and pushes the ball plug away from its original position, allowing the ball plug to rotate into the empty space of the upper base, at this time the channel opening of ball plug is slanted and is no longer facing the needle cannula, the ball plug does not move in parallel and the empty space is designed for the ball plug to rotate.

3. A syringe as recited in claim 1, wherein the lower base of the needle locking base and the bottom part of the connecting base of the barrel can be fabricated into one piece.

4. A syringe as recited in claim 1 wherein the needle locking base is a single unit, the empty space is a post shape having a channel to link to the internal space of the plunger, the rear portion of the empty space has a post plug which also has a channel opening, such channel opening is offset from the center of the post plug, when the projected member moves forward, it pushes the post plug into the front of the empty space and seals off the channel to the needle cannula.

5. A syringe as recited in claim 1 wherein the needle locking base and the connecting base can be securely joint together by using ultrasound technology.

6. A syringe as recited in claim 1 wherein the needle locking base and the connecting base can be securely assembled together by using epoxy glue.

* * * * *